United States Patent [19]
Domagala et al.

[11] Patent Number: 6,057,315
[45] Date of Patent: May 2, 2000

[54] ANTIBACTERIAL AGENTS

[75] Inventors: John Michael Domagala, Canton; Edmund Lee Ellsworth, Brighton; Michael Andrew Stier, Ypsilanti, all of Mich.; Liren Huang, Edmonton, Canada; Ronald George Micetich, Sherwood Park, Canada; Rajeshwar Singh, Edmonton, Canada; Stephen Keith Wrigley, Woodburn, United Kingdom; Shouming Wang, Langley, United Kingdom; Michael Roe, Cippenham, United Kingdom; David Michael Thornton, Reading, United Kingdom

[73] Assignee: Warner-Lambertt Company, Morris Plains, N.J.

[21] Appl. No.: 09/269,492

[22] PCT Filed: Dec. 5, 1997

[86] PCT No.: PCT/US97/22356

§ 371 Date: Mar. 29, 1999

§ 102(e) Date: Mar. 29, 1999

[87] PCT Pub. No.: WO98/25932

PCT Pub. Date: Jun. 18, 1998

Related U.S. Application Data

[60] Provisional application No. 60/032,144, Dec. 9, 1996.

[51] Int. Cl.[7] .................. A61K 31/517; A61K 31/536; C07D 487/04; C07D 498/04; C07D 513/04

[52] U.S. Cl. .................. 514/224.5; 514/229.8; 514/267; 544/32; 544/89; 544/252

[58] Field of Search .................. 544/32, 89, 252; 514/224.5, 229.8, 267

[56] References Cited

FOREIGN PATENT DOCUMENTS 97 234 86 7/1997 WIPO.

OTHER PUBLICATIONS

Chu et al., "New Directions in Antibacterial Research", *J. Med. Chem.*, 1996, 39:20, 3853–3865.
Cruz et al., "APHE–3 and APHE–4, Two New Pyrazoloisoquinolinone Antibiotics Produced by *Streptoverticillium griseocarneum* NCIMB 40447", *J. Antibiotics*, 1996, 49:7, 700–702.
Takacs and Helle, "A Removable Auxiliary For Amidomercuration Reactions: The Stereoselective Preparation of Substituted N–Acyl Pyrrolidines and Piperidines", *Tetrahedron Letters*, 1989, 30:52, 7321–7324.
Takacs et al., "The Magnitude of the Sterodirecting Effect of an Allylic Alkoxy–Substituent in an Amidomercuration Cyclization", *Tetrahedron Letters*, 1990, 31:47, 6765–6768.
Tafel and Bates, "Preparation of Pyrrolo[2,1–b][1,3] benzothiazin–9–ones via Intramolecular Sulfenylation of an N–Acylpyrrole", *J. Org. Chem.*, 1992, 57, 3676–3680.

*Primary Examiner*—Mukund J. Shah
*Assistant Examiner*—V Balasubramanian
*Attorney, Agent, or Firm*—Elizabeth M. Anderson

[57] ABSTRACT

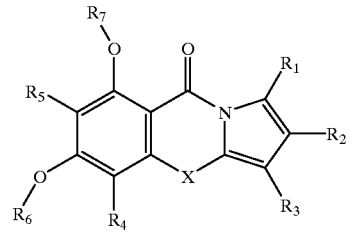

(I)

Described are antibacterial agents of formula (I): X is O, S or N—$R_8$; $R_1$, $R_2$, $R_3$ and $R_8$ are independently H, straight or branched alkyl of 1–6 carbons, cycloalkyl of 3–6 carbons, alkenyl or alkynyl of from 2 to 6 atoms, R heterocyclic ring of from 5–8 atoms with 1–3 heteroatoms as nitrogen, oxygen or sulfur, or phenyl, all of which rings may be optionally substituted up to 3 times by halogen, OR, $NR_2$, NR'COR', CN, $CO_2R'$ or $CONR_2'$, halogen, CN, $CO_2R$, COR, CON$(R)_2$, CON$(R")_2$, SR, SON, $SCO_2R$ or SCON$(R)_2$; $R_4$ is H, straight or branched alkyl of from 1–6 carbon atoms, alkenyl or alkynyl of from 2 to 6 atoms, heterocyclic ring of from 5–8 atoms with 1–3 heteroatoms as nitrogen, oxygen or sulfur or phenyl, all of which rings may be optionally substituted up to 3 times by halogen, OR, $NR_2$, NR'COR', CN, $CO_2R'$ or $CONR_2'$, halogen, CN, $NO_2$, $N(R)_2$, NRCOR, NRCOR", COR, $CO_2R$, CON$(R)_2$, CON$(R")_2$, NRCON$(R)_2$, $NRCO_2R$; $R_5$ is 1–6 straight or branched alkyl, a cycloalkyl of 3–6 carbons, alkenyl or alkynyl of from 2 to 6 atoms, heterocyclic ring of from 5–8 atoms with 1–3 heteroatoms as nitrogen, oxygen or sulfur or phenyl, all of which rings may be optionally substituted up to 3 times by halogen, OR, $NR_2$, NR'COR', CN, $CO_2R'$ or $CONR_2'$, halogen, OR, $N(R)_2$, NRCOR, NRCOR", COR, CON$(R)_2$, CON$(R")_2$, SR or $SO_2R$; $R_6$, $R_7$ are independently H, straight or branched alkyl of 1–6 carbons, cycloalkyl of 3–6 carbons, COR, COR", $SO_2NR_2$, $CONR_2$ and these may be optionally substituted by any of the groups listed for $R_5$; R is H, straight or branched alkyl of 1–6 carbon atoms, cycloalkyl of from 3–6 carbon atoms, heterocyclic ring of from 5–8 atoms with 1–3 heteroatoms as nitrogen, oxygen or sulfur, or pheny, all of which may be optionally substituted by halogen, OR', $NR'_2$, NR'COR', CN, $CO_2R'$, $CONR'_2$, R' is H, alkyl of from 1–3 carbon atoms or Ph; R" is part of a naturally occurring amino acid connected via an amide or acyl bond as determined by the formula; halogen is any one of fluoro, chloro, bromo or iodo; or a pharmaceutically acceptable salt.

24 Claims, No Drawings

ANTIBACTERIAL AGENTS

This is a 371 of PCT/US97/22356 filed Dec. 5, 1997 which claims the benefit of provisional application No. 60/032,144 filed Dec. 9, 1996.

The invention pertains to anti-bacterial materials which contain a 4-oxo-1,3-benzoxazine ring structure.

BACKGROUND OF THE INVENTION

Due to ever increasing antibiotic resistance, new anti-bacterials of novel structure have become very important to the treatment of bacterial infections (J. Med. Chem 39, 3853, 1996).

Kinoshita (J. Antibiotics 48, 437, 1995) has revealed various pyralomicins.

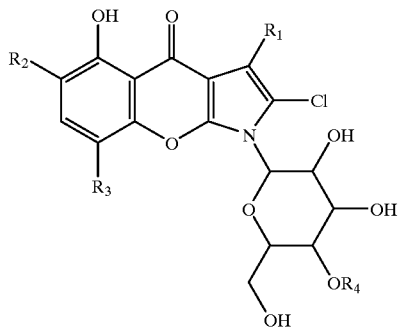

These compounds were isolated from *Microtetraspora spiralis* and display good activity vs *Micrococcus luteus*, but relatively poor activity versus *Staphylococcus aureus*. The compounds all contain the sugar moiety and are thus higher molecular weight.

Soliveri reveals pyrazaloisoquinolenones from *Streptoverticillium griseocarnum* (J. Antibiotics 49, 700, 1996).

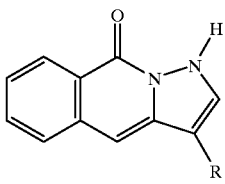

These compounds show poor activity versus Staphylococci and contain a ring system substantially different than that shown in Formula I.

Saturated fused ring systems have been reported (Tet. Lett 30, 7321, 1989; and 31, 6765, 1990) where the pyrrolidine and piperidine rings are fully saturated rather than aromatic. No biological activities were reported.

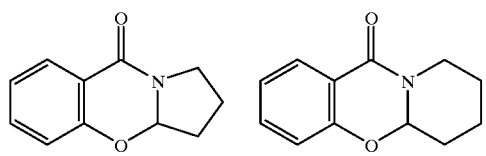

A method of preparation has been disclosed where a S replaces the oxygen of the benzoxazine ring system (J. Org. Chem. 57, 3676, 1992). The phenyl ring is not substituted and no biological activity is disclosed.

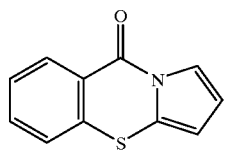

Sckrob et al. disclose ring systems where nitrogen has replaced the benzoxazine ring oxygen (J. Gen. Chem. USSR 38, 1970, 1968); no biological activities were revealed.

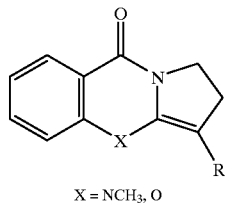

X = NCH₃, O

SUMMARY OF THE INVENTION

Described are compounds of Formula I

FORMULA I

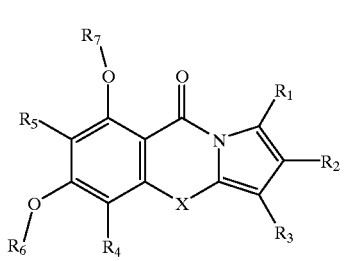

X is O, S or N—$R_8$;

$R_1$, $R_2$, $R_3$ and $R_8$ are independently H, straight or branched alkyl of 1–6 carbons, cycloalkyl of 3–6 carbons, alkenyl or alkynyl of from 2 to 6 atoms, heterocyclic ring of from 5–8 atoms with 1–3 heteroatoms as nitrogen, oxygen or sulfur or phenyl, all of which rings may be optionally substituted up to 3 times by halogen, OR, $NR_2$, NR'COR', CN, $CO_2R'$ or $CONR_2'$, halogen, CN, $CO_2R$, COR, CON$(R)_2$, CON$(R")_2$, SR, SON, $SCO_2R$ or SCON$(R)_2$;

$R_4$ is H, straight or branched alkyl of from 1–6 carbon atoms, alkenyl or alkynyl of from 2 to 6 atoms, heterocyclic ring of from 5–8 atoms with 1–3 heteroatoms as nitrogen, oxygen or sulfur or phenyl, all of which rings may be optionally substituted up to 3 times by halogen, OR, $NR_2$, NR'COR', CN, $CO_2R'$ or $CONR_2'$, halogen, CN, $NO_2$, N$(R)_2$, NRCOR, NRCOR", COR, $CO_2R$, CON$(R)_2$, CON$(R")_2$, NRCON$(R)_2$, $NRCO_2R$;

$R_5$ is 1–6 straight or branched alkyl, a cycloalkyl of 3–6 carbons, alkenyl or alkynyl of from 2 to 6 atoms, heterocyclic ring of from 5–8 atoms with 1–3 heteroatoms as nitrogen, oxygen or sulfur or phenyl, all of which rings may be optionally substituted up to 3 times by halogen, OR, $NR_2$, NR'COR', CN, $CO_2R'$ or
  CONR₂', halogen, OR, N$(R)_2$, NRCOR, NRCOR", COR, CON$(R)_2$, CON$(R")_2$, SR or $SO_2R$;

$R_6$, $R_7$ are independently H, straight or branched alkyl of 1–6 carbons, cycloalkyl of 3–6 carbons, COR, COR", $SO_2NR_2$, $CONR_2$ and these may be optionally substituted by any of the groups listed for $R_5$;

R is H, straight or branched alkyl of 1–6 carbon atoms, cycloalkyl of from 3–6 carbon atoms, heterocyclic ring of from 5–8 atoms with 1–3 heteroatoms as nitrogen, oxygen or sulfur, or phenyl all of which may be optionally substituted by halogen, OR', NR'$_2$, NR'COR', CN, CO$_2$R', CONR'$_2$;

R' is H, alkyl of from 1–3 carbon atoms or Ph;

R" is part of a naturally occurring amino acid connected via an amide or acyl bond as determined by the formula;

halogen is any one of fluoro, chloro, bromo or iodo;

or a pharmaceutically acceptable salt.

The invention is also concerned with treating a mammal in need thereof comprising administering to said mammal an effective antibacterial amount of the compound of Formula I.

The invention is also concerned with pharmaceutical compositions utilizing the compounds of claim 1 or pharmaceutically acceptable salts thereof.

DESCRIPTION OF PREFERRED EMBODIMENTS

The compounds of the present invention may be prepared according to the chemistry outlined in the following Schemes.

[Scheme 1]

The phenolic groups in 1 may be alkylated for purposes of modification or protection as outlined. Using kinetic control, 1 may be selectively converted to the monoalkyl derivative 2. Such kinetic control may be attained by using limited quantities of irreversible bases. Limited quantities refers to 0.9 to 1.2 equivalents of base. Irreversible bases would include sodium or potassium hydride, alkyl lithiums like butyl lithium, LDA (lithium diisopropylamide) and the like. Reactions are generally carried out in two discrete steps in etheral or nonprotic solvents. The first step, in which the proton of the phenol is extracted, generally occurs at −78°–50° C. The second step, which involves the actual alkylation of the phenol anion, is carried out at −50°–100° C.

Using thermodynamic control, the dialkyl ether 3 may be obtained. Thermodynamic control is attained by the use of excess, equilibrating bases such as sodium, potassium or cesium carbonates, tertiary alkylamines, pyridine or DBU. Excess refers to any amount of base exceeding two equivalents. Typical solvents would include DMF, acetone, or acetonitrile and typical temperatures are 25°–150° C.

The alkylation reaction may also be performed in discrete steps using kinetic conditions to introduce R', followed by a subsequent addition leading to the R" ether 4. If the R' group is benzyl, methyl, or another group that may be selectively removed (H$_2$/catalyst for benzyl and BBr$_3$ or LiI$_2$ for methyl), then compounds 5 may be obtained.

[Scheme 2]

Similar to the alkylation chemistry, the phenols of 1 may be acylated as shown in Scheme 2. With excess acylating agent and long reaction times, diacylation to 6 is preferred. Limiting the acylating agent to 0.9–1.2 equivalents and/or employing shorter reaction times, 0.5–2 hours, permits monoacylation to predominate giving 7. Typical solvents are dichloromethane, toluene, benzene, and the like. Reaction temperatures are typically 10°–150° C. The acyl groups may be chosen to modify the physical properties of 1 or to act as prodrugs by deacylation through acid or enzymatic mechanisms. While Scheme 2 shows selective acylation of the C$_7$ phenol, selective acylation of the C$_5$ phenol can be achieved according to Scheme 3. In this case, the C$_7$ phenol is reacted first by alkylation (Scheme 1) or acylation (Scheme 2) to give 8, then the C$_5$ phenol is reacted to produce 9 [Scheme 3]. The C$_7$ phenol is then deprotected to give 10. The protecting groups may include methyl, benzyl, p-methoxy benzyl and the like, which may be removed by BBr$_3$ or hydrogenation. Certain reactive acyl groups could also be employed as protecting groups, such as trifluoroacetate and the like, which could readily be removed with mild base at pH 9–11 in water or aqueous alcohol.

[Scheme 4]

The introduction of the R$_4$ group may be accomplished through standard electrophilic aromatic substitution reactions well known in the art. In such a way, the compounds 11 are converted to 12. Nitrations, for example, may be conducted with nitric acid in sulfuric acid at ratios of 1:10 to 1:15 at temperatures of 10°–100° C. Alternatively nitric acid or potassium nitrite may be employed in acetic acid at temperatures of 10°–110° C. Likewise, chlorinations (b), brominations (c), formylations (d) and acylations (f) may all be performed according to conditions known in the art using typical solvents. Such reactions are described in *Organic Synthesis* volumes 1–5 and in *Reagents for Organic Synthesis* (Fieser and Fieser). Under basic conditions, the phenolic groups are ionized, the reaction of R$_4$+ is greatly facilitated to the possible exclusion of the nucleophilic sites.

Once the R$_4$'s are introduced by electrophilic aromatic substitution, certain other modifications to R$_4$ may be carried out. The nitro groups may be reduced by H$_2$ and a number of catalysts, such as Raney Nickel or Pd. The NO$_2$ group may also be reduced by metals such as tin or iron in acids such as HCl. Likewise, the formyl group or acyl group may be oximated with hydroxylamine hydrochloride in pyridine or alcohol with added inert base, at temperatures of 25°–100° C. The OH of the CH$_2$OH in 12e may be reacted to form a tosylate or other leaving group permitting displacement with halide, azide, cyanide and the like. Furthermore, the amines produced from the nitro group may be diazotized and replaced by F, Cl, Br, CN and OH by reactions well known for diazonium salts in the art. In any of the reactions described, the phenolic groups may be protected by the means shown in Schemes 1–3.

The R$_4$ groups may alternatively be added early in the synthesis of the compounds of the invention. In Scheme 5, the trialkoxy acid 13 may be converted to 14 using electrophilic substitution as described above, or alternatively R$_4$ may be introduced by anion chemistry [Scheme 5]. In this case, the acidity of the proton between the two alkoxy groups in 13 is exploited by reaction with strong bases such as LDA, t-butyl lithium, n-butyl lithium, and the like, in solvents such as ether or THF. The temperatures for such reactions are generally −78°14 30° C. Once the anions of 13 have formed, they are quenched with electrophiles R$_4$X, which may represent alkyl halides, acyl groups, or other groups that are known to react with anions such as ethyl carbonate for example, to give a carboxylic acid ester, CO$_2$Et. With 14 in hand, the carboxylic acid may be activated by conversion to an acid chloride, a mixed anhydride, or an imidazolide by standard conditions. For example, the acid chloride may be formed by reaction of 14 with (COCl)$_2$ in an inert solvent such as dichloromethane, hexane, or benzene, at temperatures of 15°–100° C. Often, a catalytic amount of DMF may be added to increase the rate of reaction. Alternatively, SOCl$_2$ or phosgene may be employed. Activated esters such or mixed anhydrides may also be employed. For example, isobutyl chloroformate may be reacted with 14 in the presence of an inert base such as N-methylmorpholine to give a mixed anhydride. Typical solvents are dichloromethane or ether and typical temperatures are −10°–25° C. The acid chlorides (or mixed anhydrides) 15 are then reacted with the appropriately substituted 2-bromopyrrole and an inert base to give 16. This reaction is performed in inert solvents such as dichloromethane, benzene, or toluene, and reaction temperatures may be 25°–100° C. Inert bases include triethyl amine, DBU and the like. The protecting group in 16 is then removed to permit cyclization of the phenol-pyrrole to give 17. The cyclization is generally performed using sodium methoxide and CuBr in polar solvents such as methanol, DMF and the like at temperatures of 25°–100° C.

[Scheme 6]

Alternatively, the activated acid 15 may be reacted with a substituted pyrrole to give 16a. Oxidative cyclization of 16a is effected using Palladium acetate with a large excess of LiCl at 125° C. The LiCl is used in 5 to 50 equivalents and one equivalent of $Pd(OAc)_2$ is employed. The reaction is run in a sealed vessel at 100° C. to 150° C. in THF with consolvents added such as dioxane, DMF, and the like for solubility purposes.

The compounds 13 employed in Scheme 5 may in turn be prepared from 18 according to Scheme 6. The commercially available compound 18 is suitably protected to give 19. Such protection may include such groups as benzyl, p-methoxy benzyl, or even methyl where the protecting group may be released with acid, $H_2$, $BBr_3$, $MgI_2$ and the like. Compound 19 may then be reacted under electrophilic conditions or anion conditions described above to introduce the $R_5$ substituent in 13. Alternatively, $R_5$ may be introduced directly into 20 by conditions described above to give 21, which may then be carboxylated with alkyl lithium or LDA followed by treatment with carbon dioxide as a gas or in the form of dry ice. Reactions with the alkyl lithiums and LDA are generally carried out with temperatures of −78°–0° C. in ether or THF.

[Scheme 7]

Alternatively, $R_5$ may be introduced after $R_4$ as shown in Scheme 7. The introduction of $R_5$ via electrophilic or anion chemistry follows the same procedures as outlined for Scheme 5. The compound 22 is then converted to 17 as described above.

Yet another alternative to introduction of $R_5$ involves employing an $R_5$ type group as a protecting group as shown in 17a using classical Claisen or Fries type rearrangements, $R_5$ is delivered to the $R_5$ position in 17. Such rearrangements are well known in the art and are carried out with acid or thermal conditions.

There is in fact great flexibility in the Schemes 5–7 such that $R_4$ or $R_5$ may be introduced in a sequence that is most compatible and high yielding depending on the nature of $R_4$ and $R_5$.

[Scheme 8]

The 2-bromopyrroles may be prepared from the substituted pyrrole 23 and a suitable brominating agent and initiator such as AIBN according to Scheme 8. This reaction is performed at low temperatures of −78°—−10° C. in ether, THF, or hydrocarbon solvent. The 2-bromopyrroles are often unstable and are used in solution without purification. The pyrroles 23 are often commercially available or can be prepared according to multiple procedures known in the art.

[Scheme 9]

Alternatively, the groups $R_1$–$R_3$ may be introduced and modified after the pyrrole cyclization has occurred. In Scheme 9, the natural product 2-chloro-5,7-dihydroxy-6-propyl-9 oxa-3a-aza-cyclopenta[b]naphthalene-4-one may be dechlorinated with $H_2$/RaNi at RT in alcoholic solvents and short reaction times. Groups may be introduced by electrophilic chemistry such as exemplified with N-chlorosuccinamide in chloroform to give 27, or with chlorosulfonylisocyanate with water workup to provide compounds 28. The reactive 2-pyrrole position may be converted to an anion by LDA and then captured by silanes such as trimethyl silyl chloride to give 29, which may be further reacted at other positions by electrophilic chemistry well known for pyrroles in the art to give compounds 30. The silyl group may then be removed by fluoride ion to give 31 using CsF or other fluoride salts in solvents such as DMF or DMSO.

Compounds of the invention where X of formula I is sulfur or nitrogen may be prepared according to Schemes 10 and 11. Commercially available 32 may be reacted with 20–60 equivalents of ammonium hydroxide in water at elevated temperatures for several days. Usually 40 equivalents at 100° for 3 days gives 33 in yields of >50%. Compound 33 is purified by conversion to a nitrogen derivative like BOC or benzyloxy carbonyl. Such nitrogen derivatives are commonly used in nitrogen protection and are well known in the art. The protected nitrogen compound can be further embellished to compound 34 in a manner similar to Schemes 6 and 7. Compound 34 can be reacted with oxalyl chloride in THF, toluene, or other inert solvents. Upon heating, the oxalyl amide is cyclized to 35. Temperatures are generally reflux of the solvent used. Alternatively, Lewis acid catalysts such as $AlCl_3$ can be employed. Compound 35 may be oxidized by hydrogen peroxide in alcohol to yield the substituted anthanilic acid 36. Compound 36 may be diazotized using any of the conditions well known in the art. These would include using sodium nitrite in HCl or flouroboric acid, as well as t-butyl nitrite. The diazonium ion may be reacted with cuprous thiocyanate to give 37. Such reactions are generally carried out in water or water alcohol at 0°–50° C. The thiocyanate may be reduced with a variety of commonly used reducing agents like borohydride, $H_2$ and the like. Dithiothreitol (DTT) is particularly valuable because of its mildness toward other function groups. Such reductions with DTT are carried out at 0°–50° C. in water, water-dioxane, water-THF or water-alcohol mixes. The reduced thiol is then alkylated with methyl iodide or ethyl iodide or other similar alkylating agents such as, dimethyl sulfate to give 38 where $R_A$ is ethyl or methyl. Such alkylations usually are performed in THF, DMF or other inert solvents. Bases such as NaH, $K_2CO_3$ or KH are employed at temepratures of 25°–125° C. The acid function in 38 is then activated and reacted with the pyrrole as described in Scheme 5 to give compound 39. Oxidative cyclization is effected by oxidizing the sulfur to the suffoxide by certain oxidizing agents such as sodium periodate, or meta chloroperbenzoic acid. The suffoxide is heated or treated with acids to effect the cyclization to the desired 40. The steps 38 through 40 are known in the art and were published to make these identical ring systems (J. Org. Chem 57, 3676, 1992). Alternatively, compound 38 may be prepared from the commercially available 3,5-dimethoxy fluorobenzene, 41, which may be embellished to the flouro acid as in 38 where the $SR_A$ is a flouro group. The flouro acid may be reacted with $R_AS$ to give 38.

Compounds where X is nitrogen are prepared in Scheme 11 and use intermediate 36 from Scheme 10 as a starting material. The acid is activated by any of the methods in Scheme 5. Carbonyl diimidazole is particularly useful for activating the acid. This activation may take place in THF, dioxane, THF/DMF or other inert solvents at 0°–80°. Once activated, the pyrrole may be added to produce the amide 37. Either of the cyclization methods described in Scheme 5 may be employed to give the desired 43.

Alternatively in both Schemes 10 and 11, the $R_5$ group may be delivered via a Claisen rearrangement or a Fries rearrangement as shown in Scheme 7.

Alternative Scheme 12 can be used to introduce unsaturation (alkenyl or alkynyl groups) or ring structures (heterocyclic or aromatic) into the basic ring structure. See: R. F. Heck Org. React. 1982, 27, 345; J. K. Stille, Ange. Chem. Int. Ed. Engl. 25, 508, 1986.

EXAMPLE A
2-Bromopyrrole

To 1.5 g (22 mmol) of pyrrole in 60 mL of dry THF was added 40 mg of azoisobutyronitrile (AIBN) at −78° C. After 5 min 3.19 g (11.2 mmol) of 1,3-dibromo-5,5-dimethylhydantoin was added over 20 min. After 2 hr the solution was filtered into 120 mL of dry $CH_2Cl_2$ at −78° C. Solutions of 2-bromo pyrrole prepared in this way are used in subsequent reactions.

EXAMPLE B
N-(2-Methoxybenzoyl)-2-bromopyrrole

To the stirred solution of 2-bromo-pyrrole (22.3 mmol) in 60 mL of dry THF and 120 mL of $CH_2Cl_2$ at −78° C. in an atmosphere of nitrogen, was added triethylamine (6.22 mL, 44.6 mmol) followed immediately by dropwise addition of a solution of 2-methoxybenzoyl chloride (5.0 mL, 33.6 mmol) in 40 mL $CH_2Cl_2$. The reaction mixture was stirred overnight while it was allowed to warm to room temperature. The mixture was washed with water and brine, dried ($Na_2SO_4$) and concentrated in vacuo at room temperature. The crude product was purified by chromatography on triethylamine-treated neutral silica, using EtOAc-Hex (5:95) as the eluent, to give 3.81 g of the title compound as a colorless oil. $^1$H NMR ($CDCl_3$) δ: 7.58–7.36 (2 H, m), 7.10–6.86 (3 H, m), 6.36 (1 H, dd, J=3.5, 1.8), 6.16 (1 H, t, J=3.5), 3.78 (3 H, s).

EXAMPLE C
N-(2-Hydroxybenzoyl)-2-bromopyrrole
Method A

To a solution of N-(2-methoxybenzoyl)-2-bromopyrrole (1.40 g, 5 mmol, from Example B) in 30 mL of dry benzene was added 5 mL of a solution of magnesium iodide etherate [made from magnesium (2 g), iodine (10 g), dry ether (12.5 mL), and dry benzene (25 mL)], and the solution was heated under reflux in an atmosphere of nitrogen overnight. The cooled solution was diluted with 60 mL of $CH_2Cl_2$, and was washed with sat. aq. $NH_4Cl$, sat. aq. $NaHCO_3$, and brine. The organic layer was dried ($Na_2SO_4$) and concentrated in vacuo to give 1.26 g of the title compound. $^1$H NMR ($CDCl_3$) δ: 10.35 (1 H, s), 7.61–7.49 (2 H, m), 7.20–6.90 (3 H, m), 6.47 (1 H, dd, J=3.5, 1.8), 6.29 (1 H, t, J=3.5).
Method B To a stirred solution of N-(2-methoxybenzoyl)-2-bromopyrrole (0.28 g, 1 mmol, from Example B) in 30 mL of $CH_2Cl_2$ at 0° C. in an atmosphere of nitrogen was added boron tribromide (0.10 mL, 1.1 mmol). The reaction mixture was stirred at 0° C. for 30 min. The reaction was terminated by careful addition of 30 mL of sat aq. $NaHCO_3$. The layers were separated, the organic layer was washed with water and brine, dried ($Na_2SO_4$) and concentrated in vacuo to give 0.21 g of the title compound.

EXAMPLE D
N-(2,4-Dimethoxybenzoyl)-2-bromopyrrole
Following the procedure of Example B, 2,4-dimethoxybenzoyl chloride (6.74 g, 3.36 mmol) and 2-bromopyrrole (22.4 mmol) gave 3.12 g of the title compound: mp 81–82° C.; $^1$H NMR ($CDCl_3$) δ: 7.42 (1 H, t, J=8.4), 6.99 (1 H, t, J=1.8), 6.70–6.45 (2 H, m), 6.42–6.25 (1 H, m), 6.16 (1 H, t, J=3.5), 3.87 (3 H, s), 3.77 (3 H, s).

EXAMPLE E
N-(2-Hydroxy-4-methoxybenzoyl)-2-bromopyrrole
Following the procedure from Example C method A, (2,4-dimethoxybenzoyl)-2-bromopyrrole (1.55 g, 5 mmol, from Example D) and magnesium iodide etherate (5 mL) gave 1.28 g of the title compound. $^1$H NMR ($CDCl_3$) δ: 10.96 (1 H, s), 7.48 (1 H, d, J=8.4), 7.06–6.97 (1 H, m), 6.60–6.32 (3 H, m), 6.28 (1 H, t, J=3.5), 3.90 (3 H, s).

EXAMPLE F
2,4,5-Trimethoxybenzoyl Chloride

To a suspension of 2,4,5-trimethoxybenzoic acid (2.12 g, 10 mmol) in dry 10 mL benzene was added thionyl chloride (4.4 mL, 60 mmol). The reaction mixture was stirred at 70° C. for 5 hr. The solvent was evaporated in vacuo. The residue was washed with hexane to give 2.07 g of the title compound which was used for the next step without further purification. $^1$H NMR ($CDCl_3$) δ: 7.65 (1 H, s), 6.50 (1 H, s), 4.05 (3 H, s), 3.97 (3 H, s), 3.86 (3 H, s).

EXAMPLE G
N-(2,4,5-Trimethoxybenzoyl)-2-bromopyrrole
Following the procedure for Example B, 2,4,5-trimethoxybenzoyl chloride (1.38 g, 6 mmol) and 2-bromopyrrole (4 mmol) gave 0.75 g of the title compound: mp 120–121° C.; $^1$H NMR ($CDCl_3$) δ: 7.05–6.95 (2 H, m), 6.52 (1 H, s), 6.35 (1 H, dd, J=3.3, 1.8), 6.18 (1 H, t, J=3.5), 3.96 (3 H, s), 3.86 (3 H, s), 3.76 (3 H, s).

EXAMPLE H
2,4,6-Trimethoxybenzoic acid

To a stirred solution of 1,3,5-trimethoxybenzene (10.0 g, 59.4 mmol) in 150 mL of dry THF at 0° C. in nitrogen atmosphere was added 27.3 mL (68.31 mmol) of 2.5 M n-BuLi in hexane dropwise via syringe. The resulting solution was stirred at room temperature overnight. The mixture was cooled to −20° C. and 30 g of dry ice was added. Stirring was continued for 1 hr before hydrolysis with 200 mL of water. The mixture was evaporated under reduced pressure to remove THF. The aqueous phase was extracted with ether, acidified with hydrochloric acid to pH 3 and extracted with ethyl acetate. The organic layer was washed with brine, dried ($MgSO_4$) and concentrated. The solid residue was washed with ether and dried in vacuo to give 6.7 g of the title compound: mp 152–153° C. dec (lit.: 147° C. dec.; Beilsteins, 10, 1988). $^1$H NMR ($CDCl_3$): 6.16 (2 H, s), 3.91 (6 H, s), 3.86 (3 H, s).

EXAMPLE I
2-Propyl-1,3,5-trimethoxybenzene

To the stirred solution of 1,3,5-trimethoxybenzene (10.0 g, 59.4 mmol) in 150 mL of dry THF at 0° C. in nitrogen atmosphere was added 23.7 mL (59.3 mmol) of 2.5 M n-BuLi in hexane dropwise via syringe. The resulting solution was stirred at room temperature for 4 hr. The mixture was cooled to −20° C. and 1-iodopropane (6.09 mL, 62.5 mmol) was added dropwise via syringe in 10 min. After being stirred at room temperature for 14 hr and refluxed for 4 hr, the mixture was quenched with 200 mL of water, concentrated in vacuo to remove THF and extracted with ether. The organic layer was washed with water, dried ($MgSO_4$) and concentrated. The crude product was washed with hexane to give 11.07 g of the title compound: mp 48.5–49.5° C.; $^1$H NMR ($CDCl_3$): 6.13 (2 H, s), 3.80 (3 H, s), 3.79 (6 H, s), 2.52 (2 h, m), 1.44 (2 H, sex, J=7.5 Hz), 0.91 (3 H, t, J=7.5 Hz).

EXAMPLE J

3-Propyl-2,4,6-trimethoxybenzoic acid

To the stirred solution of 2-propyl-1,3,5-trimethoxybenzene (3.00 g, 14.27 mmol) in dry THF (50 mL) at 0° C. in nitrogen atmosphere was added 6.28 mL (15.7 mmol) of 2.5 M n-BuLi in hexane dropwise via syringe. After the resulting solution was stirred at room temperature for 4 hr, 20 g of dry ice was added in portions over 20 min. After 30 min 50 mL of water was added. The mixture was evaporated under reduced pressure to remove THF and the aqueous phase was extracted with ether, acidified with hydrochloric acid to pH 3, and extracted again with ethyl acetate. The organic layer was washed with brine, dried ($MgSO_4$) and concentrated. Purification of the solid residue by flash chromatography on silica column with 10% MeOH in dichloromethane provided 1.67 g of the title compound: mp 129.0–130.0° C. dec; $^1$H NMR ($CDCl_3$): 6.30 (1 H, s), 3.93 (3 H, s), 3.87 (3 H, s), 3.83 (3 H, s), 2.54 (2 H, m), 1.49 (2 H, sex, J=7.5 Hz), 0.94 (3 H, t, J=7.5 Hz).

EXAMPLE 1(A and B)

2-Chloro-8-hydroxy-6-methoxy-7-propyl-9H-pyrrolo[2,1-b][1,3]benzoxazin-9-one A, and 2-chloro-6,8-dimethoxy-7-propyl-9H-pyrrolo[2,1-b][1,3]benzoxazin-9-one B To 50 mg (0.17 mmol) of 2-chloro-6,8-dihydroxy-7-propyl-9H-pyrrolo [2,1-b][1,3]benzoxazin-9-one in 2 mL of acetone was added 282 mg (2.04 mmol) of $K_2CO_3$ and 0.38 mL (4.0 mmol) of dimethylsulfate. The mixture was refluxed overnight. It was then cooled, acidified with 1N HCl and extracted with ethyl acetate which was then dried ($Na_2SO_4$) and concentrated. The residue was purified by preparative TLC (Silica Gel: $CH_2Cl_2$). Two bands were collected, leached into $CH_2Cl_2$, and filtered. Band A gave 27 mg of material and was the monomethylated title compound A: mp 176–177° C. Band B gave 15 mg of the dimethylated title compound B: mp 163–164° C.

EXAMPLE 2

2,2'-[2-chloro-9-oxo-7-propyl-9H-pyrrolo[2,1-b][1,3]benzoxazin-6,8-diyl)bis(oxy)]-bis[methyl acetate]

To 25 mg (0.85 mmol) of 2-chloro-6,8-dihydroxy-7-propyl-9H-pyrrolo [2,1-b][1,3]benzoxazin-9-one in 1 mL of acetonitrile was added 139 mg (0.43 mmol) of $Cs_2CO_3$ and 0.019 mL (0.20 mmol) of methyl bromoacetate. The reaction was heated at 50° C. for 1 hr. It was cooled, diluted with ethyl acetate, and extracted with 1N HCl two times. The organic layer was dried ($Na_2SO_4$) and concentrated. The residue was purified by column chromatography (Silica gel hexane: EtOAc 1:1) to give 27 mg of the title compound: mp 102–103° C.

EXAMPLE 3

2-chloro-8-hydroxy-9-oxo-7-propyl-9H-pyrrolo[2,1-b][1,3]benzoxazin-6-yl dimethylsulfamate To 80 mg (0.27 mmol) of 2-chloro-6,8-dihydroxy-7-propyl-9H-pyrrolo [2,1-b][1,3]benzoxazin-9-one in 3 mL of toluene was added 0.3 mL (2.77 mmol) of dimethylsulfamylchloride and 0.066 g (0.54 mmol) of 4-dimethylaminopyridine (DMAP). The mixture was heated to 85° C. for 2 hr. It was cooled, diluted with ethyl acetate and extracted two times with 1N HCl. The organic layer was dried ($Na_2SO_4$) and concentrated. The residue was purified by preparative TLC (hexane: $CH_2Cl_2$; 1:1) to give 77 mg of the title compound mp 159–160° C.

EXAMPLE 4

2-chloro-8-hydroxy-9-oxo-7-propyl-9H-pyrrolo[2,1b][1,3]benzoxazin-6-yl-1-methyl-1H-imidazole-4-sulfonate To 51 mg (0.17 mmol) of 2-chloro-6,8-dihydroxy-7-propyl-9H-pyrrolo [2,1-b][1,3]benzoxazin-9-one in 3 mL of toluene was added 78 mg (0.43 mmol) of 1-methyl imidazole-4-sulfonylchloride and 39 mg (0.32 mmol) of DMAP. The mixture was heated to 95° C. for 10 min. It was cooled, diluted with ethyl acetate and extracted two times with water. The organic layer was dried ($Na_2SO_4$) and concentrated. The residue was purified by preparative TLC (Silica Gel, $CH_2Cl_2$) to give 67 mg of the title compound mp 202–203° C.

EXAMPLE 5

2-Chloro-6,8-dihydroxy-9-oxo-7-propyl-9H-pyrrolo[2,1-b][1,3]benzoxazine-1-carboxamide To 100 mg (0.34 mmol) of 2-chloro-6,8-dihydroxy-7-propyl-9H-pyrrolo [2,1-b][1,3]benzoxazin-9-one in 10 mL of toluene and 15 mL of $CH_2Cl_2$ was added 0.03 mL (0.34 mmol) of chlorosulfonylisocyanate at 0° C. After 15 min., the mixture was warmed to RT, stirred for 30 min., and then 2 mL of water was added. After 30 min, the solids were filtered, washed with ether and dried in vacuo to give 60 mg of the title compound: mp 250° C. dec.

EXAMPLE 6

6,8-Dihydroxy-7-propyl-9H-pyrrolo[2,1-b][1,3]benzoxazin-9-one

A solution of 60 mg (0.18 mmol) of 2-chloro-6,8-dihydroxy-7-propyl-9H-pyrrolo [2,1-b][1,3]benzoxazin-9-one in 4 mL of methanol was subjected to hydrogenation with 0.1 g Ra-Ni, 0.4 mL of 0.5N KOH in methanol, and $H_2$ at 20 psi. The mixture was diluted with ethyl acetate and extracted with 1N HCl. The organic layer was dried ($Na_2SO_4$), concentrated, and the residue purified by preparative TLC (Silica Gel: $CH_2C_2$) to give 17 mg of the title compound: mp 170–171° C.

EXAMPLE 7

9H-Pyrrolo[2,1-b][1,3]benzoxazin-9-one

To a stirred solution of (2-hydroxybenzoyl)-2-bromopyrrole (0.26 g, 1.0 mmol, from Example C) in 5 mL of dry benzene at room temperature in an atmosphere of nitrogen, was added sodium methoxide (60 mg, 1.1 mmol). After 5 min, CuBr (22 mg, 0.15 mmol) and DMF (5 mL) were added. The reaction mixture was stirred at room temperature for 1 hr, and then stirred at 100° C. overnight. The solvent was removed in vacuo, and 30 mL of $CH_2Cl_2$ was added. The solution was washed with sat. aq. $NaHCO_3$, water, and brine. The organic layer was dried ($Na_2SO_4$) and concentrated in vacuo. The crude product was purified by chromatography, using EtOAc-Hex (5:95) as the eluent, to give 51.8 mg of the title compound: mp 129–130° C. $^1$H NMR ($CDCl_3$) δ 8.28 (1 H, dd, J=6.8, 1.8), 7.76–7.67 (1 H, m), 7.40–7.25 (3 H, m), 6.49 (1 H, t, J=3.5), 5.88 (1 H, dd, J=3.5, 1.8).

EXAMPLE 8

6-Methoxy-9H-pyrrolo[2,1-b][1,3]benzoxazin-9-one

Following the procedure of Example 7 (2-hydroxy-4-methoxybenzoyl)-2-bromopyrrole (1.55 g, 5 mmol, from Example E), sodium methoxide (0.27 g, 5.0 mmol), and CuBr (0.11 g, 0.75 mmol) gave 0.21 g of the title compound: mp 128–129° C.; $^1$H NMR (CDCl$_3$) δ: 8.18(1 H, d, J=8.9), 7.30–7.24 (1 H, m), 6.90 (1 H, dd, J=8.9, 2.4), 6.77 (1 H, d, J=2.4), 6.45 (1 H, t, J=3.5), 5.84 (1 H, dd, J=3.5, 1.8), 3.92 (3 H, s).

EXAMPLE 9

2-Chloro-6,8-dihydroxy-9-oxo-7-propyl-9H-pyrrolo[2,1-b][1,3]benzoxazine-1-carboxaldehyde To 50 mg (0.17 mmol) of 2-chloro-6,8-dihydroxy-7-propyl-9H-pyrrolo [2,1-b][1,3]benzoxazin-9-one in 5 mL of CH$_2$Cl$_2$ was added 65 mg (0.51 mmol) of chloromethylene dimethyl ammonium chloride in 1 mL of CH$_2$Cl$_2$. The reaction stirred for 2 hr. It was concentrated, dissolved in THF and 1 mL of H$_2$O was added. After 24 hr the mixture was concentrated and the residue diluted with ether, dried (Na$_2$SO$_4$) and concentrated. The residue was purified by preparative TLC (Silica Gel: hexane/EtOAc: 1:1) to give 23 mg of the title compound: mp 252° C. dec.

EXAMPLE 10

2-Chloro-6,8-dihydroxy-9-oxo-7-propyl-9H-pyrrolo[2,1-b][1,3]benzoxazine-1-carboxaldehyde, oxime To 40 mg (0.11 mmol) of the 2-chloro-6,8-dihydroxy-9-oxo-7-propyl-9H-pyrrolo[2,1-b][1,3]benzoxazine-1-carboxaldehyde made by the process of Example 9 in 5 mL of THF was added 15 mg (0.212 mmol) of hydroxylamine hydrochloride in 2 mL of water. After 14 hr the mixture was diluted with water and the resulting solids were collected by filtration to give 21 mg of the title compound: mp 201–203° C.

EXAMPLE 11

1-(Hydroxymethyl)-6,8-dihydroxy-7-propyl-9H-pyrrolo[2,1-b][1,3]benzoxazin-9-one To 40 mg (0.11 mmol) of 2-chloro-6,8-dihydroxy-9-oxo-7-propyl-9H-pyrrolo[2,1-b][1,3]benzoxazine-1-carboxaldehyde made by the process of Example 9 in 4 mL of EtOH and 4 mL THF was added 20 mg of sodium borohydride. After 15 min the mixture was diluted with H$_2$O and ethyl acetate and 1 mL of 1 N HCl with vigorous bubbling. The mixture was extracted with ethyl acetate and the organic layer dried (Na$_2$SO$_4$) and concentrated to give 48 mg of the title compound.

EXAMPLE 12

2-Chloro-1-[(dimethylamino)methyl]-6,8-dihydroxy-7-propyl-9H-pyrrolo[2,1-b][1,3]benzoxazin-9-one To 60 mg (0.20 mmol) of 2-chloro-6,8-dihydroxy-7-propyl-9H-pyrrolo [2,1-b][1,3]benzoxazin-9-one in 20 mL of CH$_2$Cl$_2$ was added 157 mg (1.22 mmol) of chloromethylene dimethylammonium chloride and the reaction stirred for 1 hr. The mixture was concentrated, diluted with 50 mL of dry MeOH and 1.0 g (15.9 mmol) of sodium cyanoborohydride was added. After 24 hr the mixture was quenched with saturated NaHCO$_3$ and the mixture extracted with ethylacetate which was dried (Na$_2$SO$_4$) and concentrated. The residue was purified by column chromatography (Silica Gel EtOAc 100% to acetone 100%) to give 50 mg of the title compound.

EXAMPLE 13

6,8-Bis(acetyloxy)-2-chloro-7-propyl-9H-pyrrolo [2,1-b][1,3]benzoxazin-9-one To 60 mg (0.20 mmol) of 2-chloro-6,8-dihydroxy-7-propyl-9H-pyrrolo [2,1-b][1,3]benzoxazin-9-one in 4 mL of toluene was added 49 mg of DMAP and 0.19 mL (2.0 mmol) of acetic anhydride. The mixture was heated to 50° C. for 24 hr. The solvent was removed and the residue purified by preparative TLC (Silica Gel: CH$_2$Cl$_2$) to give 93 mg of the title compound: mp 178–179° C.

The compounds of the present invention were tested against an assortment of gram positive and gram negative organisms using standard microtitration techniques (Cohen, et. al. *Antimicrobial Agents Chemother.* 1985, 28, 766; Heifetz, et. al. *Antimicrobial Agents Chemother.* 1974, 6, 124) and the results are given in Table 1.

TABLE 1

Antibacterial Activity

Minimum Inhibitory Concentrations ug/mL

| | Gram Negatives | | | Gram Positives | | |
|---|---|---|---|---|---|---|
| | | | | | B. | S. | S. |
| Example # | E. Coli MC4100 | E. coli B90 | E. coli Tol C | subtilis RB1 | aureus 29213 | pyogenes C203 |
| 6 | >64 | 4.0 | 2.0 | 4.0 | 2.0 | 4.0 |
| 9 | >64 | 4.0 | 2.0 | 1.0 | 4.0 | 4.0 |
| 10 | >64 | >64 | 8.0 | 32 | 32 | 16 |
| 13 | >64 | 64 | 8.0 | 8.0 | 4.0 | 4.0 |

The invention is also concerned with pharmaceutical compositions. Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and bicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. Pharma. Sci.*, 1977;66:1).

The acid addition salts of said basic compounds can be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts can be formed with metals or amines, such as alkali and alkaline earth metals or organic amines. Examples of such metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see Berge, Supra, 1977).

The base addition salts of said acidic compounds can be prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of the present invention can be prepared and administered in a wide variety of routes of administration such as parenteral, oral, topical, rectal, inhalation and the like. Formulations will vary according to the route of administration selected. Examples are oral and parenteral dosage forms. Thus, the compounds of the present invention can be administered by injection, that is, intravenously, intramuscularly, intra-cutaneously, subcutaneously, intraduodenally, or intra-peritoneally. Also, the compounds of the present invention can be administered by inhalation, for example, intranasally. Additionally, the compounds of the present invention can be administered transdermally. The following dosage forms may comprise as the active component, a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier can be a finely divided solid which is in a mixture with the finely divided active component.

In tablets, the active component can be mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component can be dispersed homogeneously therein, as by stirring. The molten homogenous mixture can be then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted for example from about 0.1 mg to 200 mg, preferably about 0.5 mg to 100 mg according to the particular application and the potency of the active component. The composition can, if desired, also contain other compatible therapeutic agents.

In therapeutic use as bacterial agents, the compounds utilized in the pharmaceutical methods of this invention can be administered at an initial dosage of about 0.01 mg to about 200 mg/kg daily (dosage amount/kg of mammal to be treated). A daily dose range of about 0.01 mg to about 50 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

Because the compounds of the invention are bacterial agents, it is believed that they inhibit bacterial histidine kinases. Bacterial histidine kinases have an important role in microorgaisms; they control the switching on and off of genes to enable the bacterium to adapt to stressful or changing conditions. The target rationale is that inhibitors of these systems could severely limit the ability of the bacteria to colonise and cause disease in the host organism, so they would have a role in the treatment of infections. The purpose of such an assay is to determine inhibition of bacterial signal transduction.

The histidine kinase used in such an assay may be a fusion of the NRIIc histidine kinase and the carboxy terminal end of the maltose binding protein, both from *E.coli*. Construction of the expression plasmid encoding the gene for this protein, and the methods of production and isolation of the purified protein is described in Karnberov, E. S. et al., Effect of mutations in *Escherichia coli glnL* (ntrB), encoding nitrogen regulator II (NRII or NtrB), on the phosphatase activity involved in bacterial nitrogen regulation. J. Biol. Chem. 269: 28294–9 (1994).

While the forms of the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

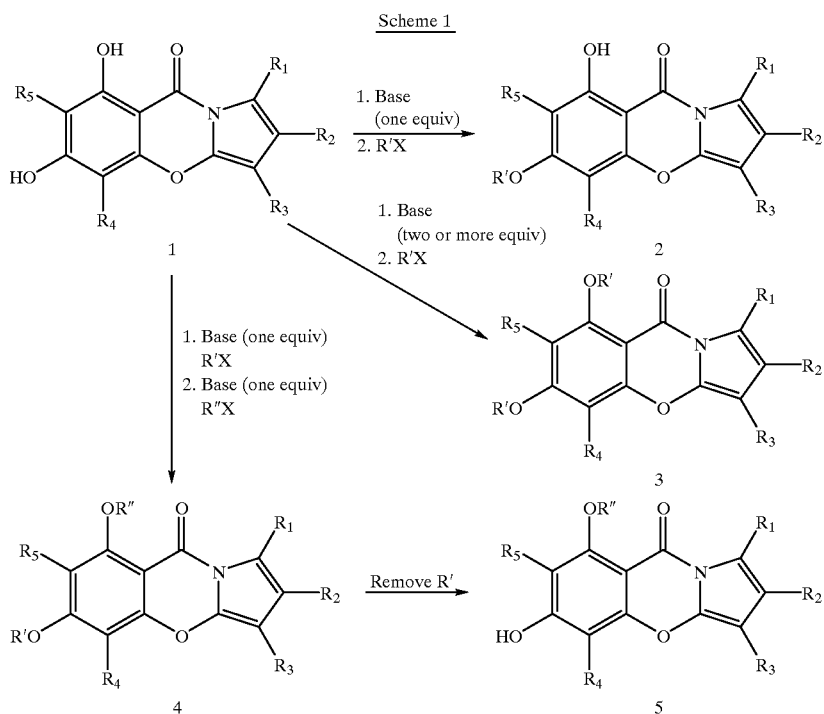

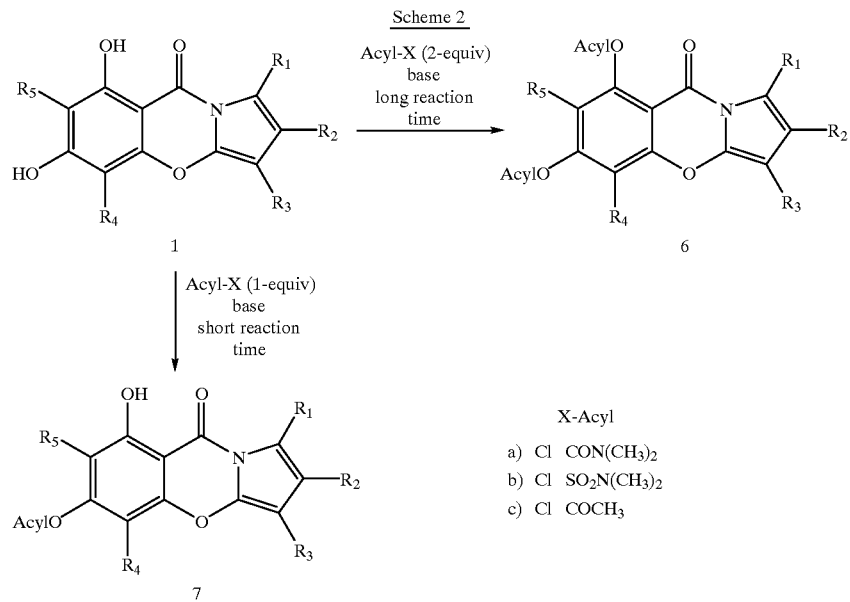
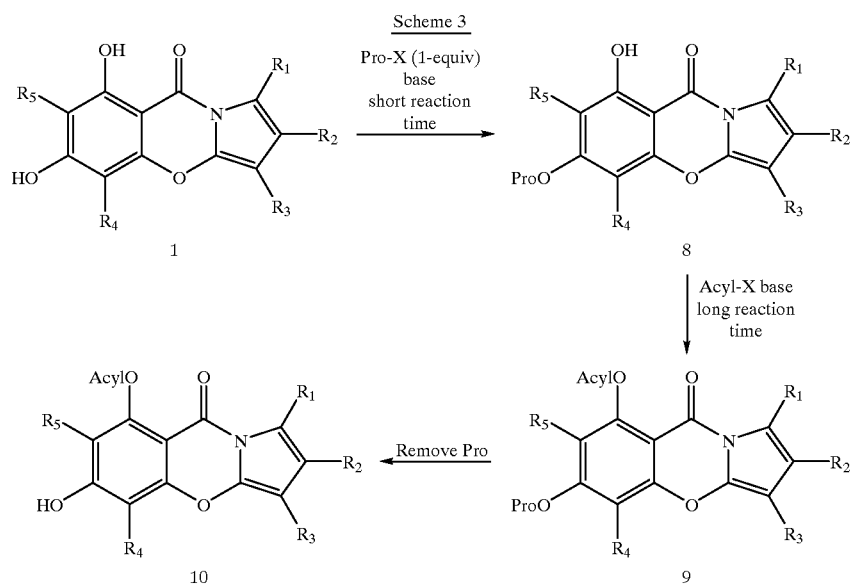
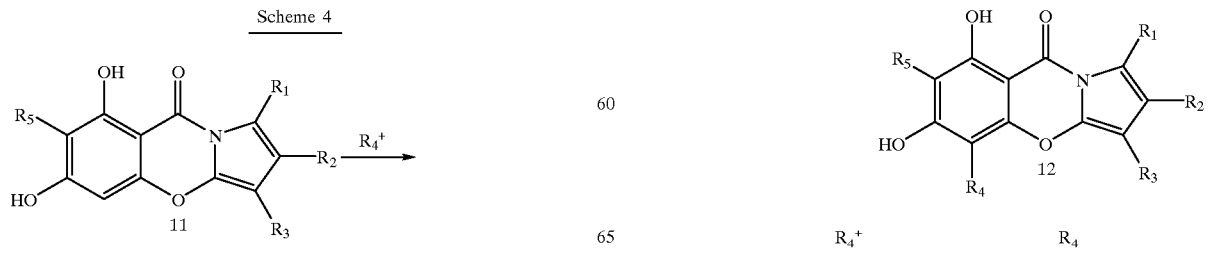

-continued
| | | |
|---|---|---|
| a) | $NO_2^+$ | $NO_2$ |
| b) | $Cl_2/FeCl_3$ | Cl |
| c) | $Br_2/FeBr_3$ or NBS | Br |
| d) | $DMF/POCl_3$ | CHO |
| e) | $CH_2O/H^+$ | $CH_2OH$ |
| f) | $CH_3COCl$ $AlCl_3$ | $CH_3CO$ |
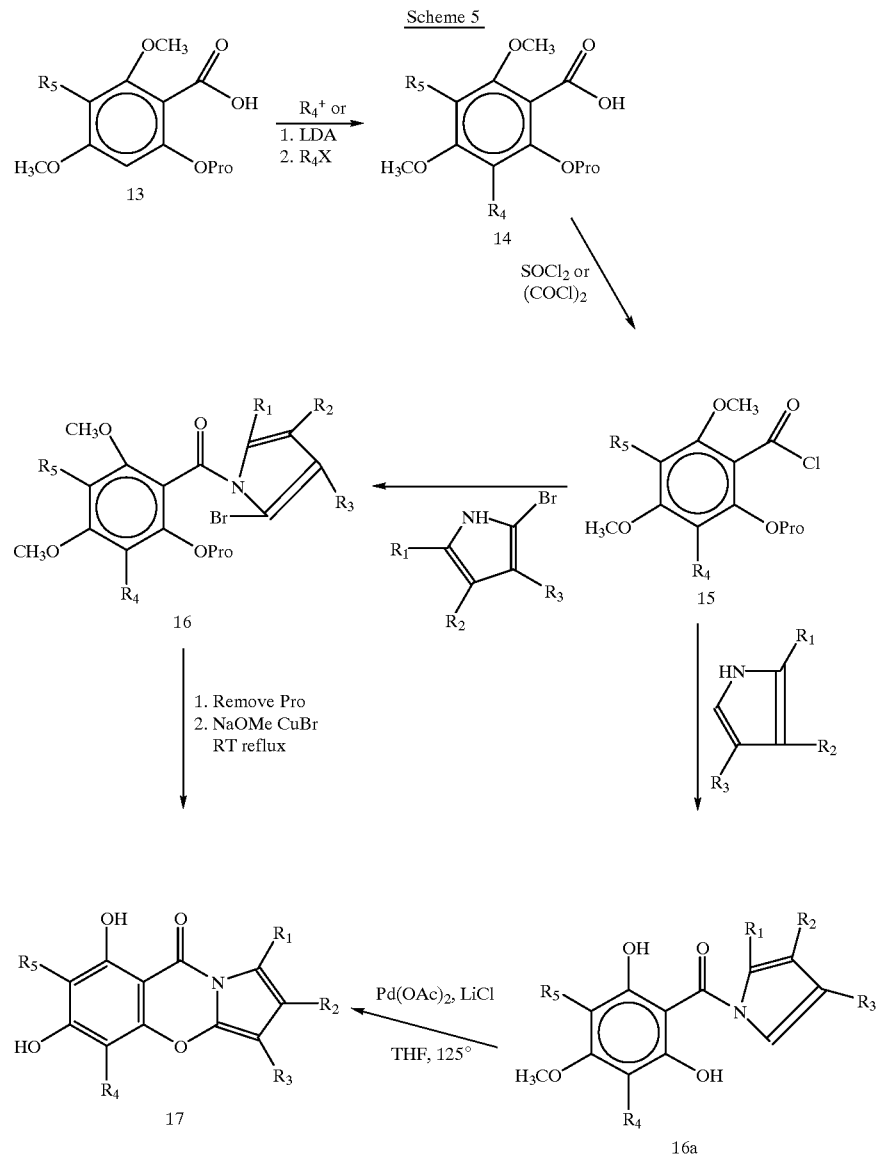
Scheme 5

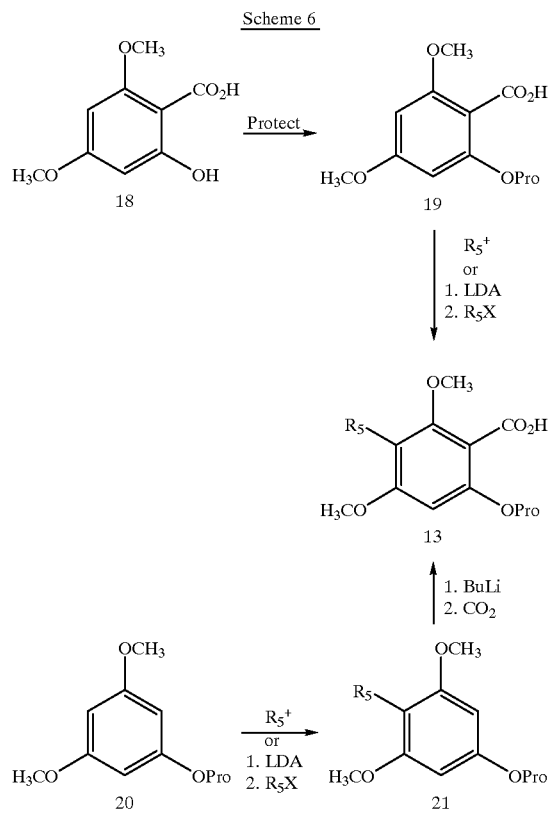
Scheme 6
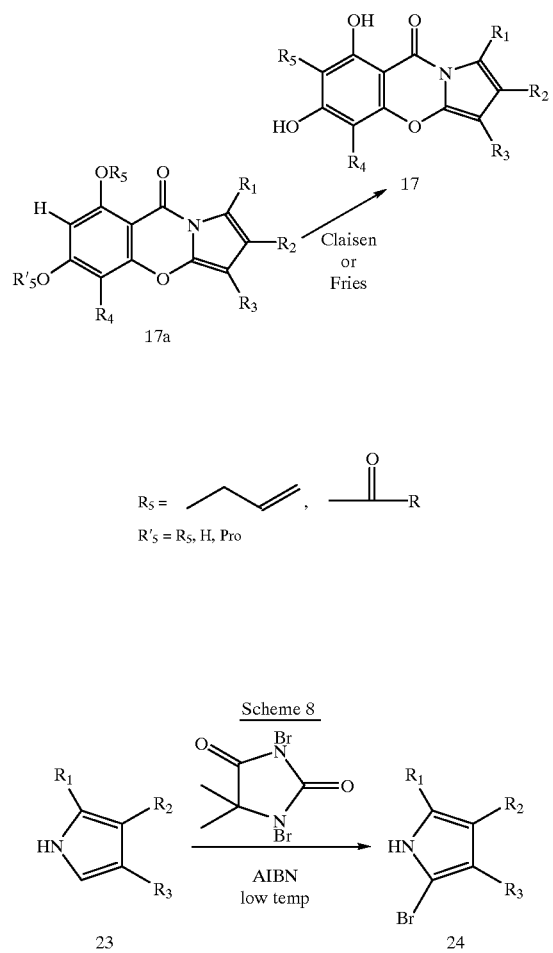
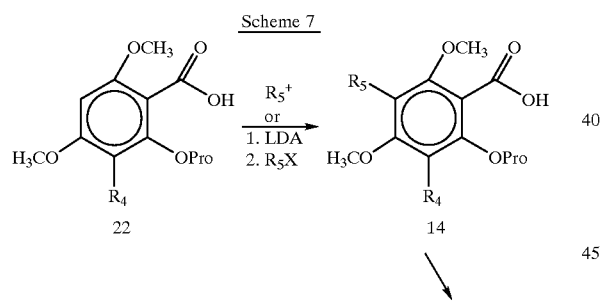
Scheme 7
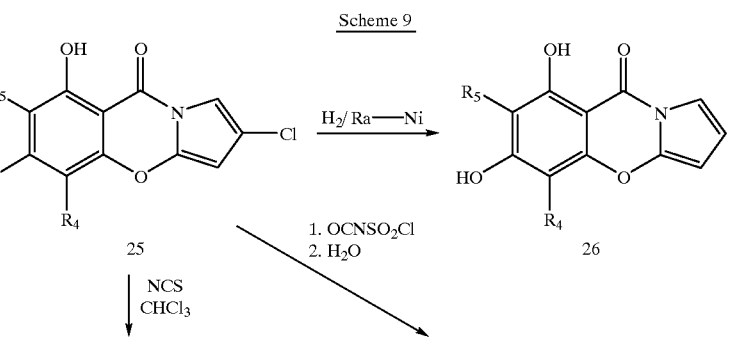
Scheme 9

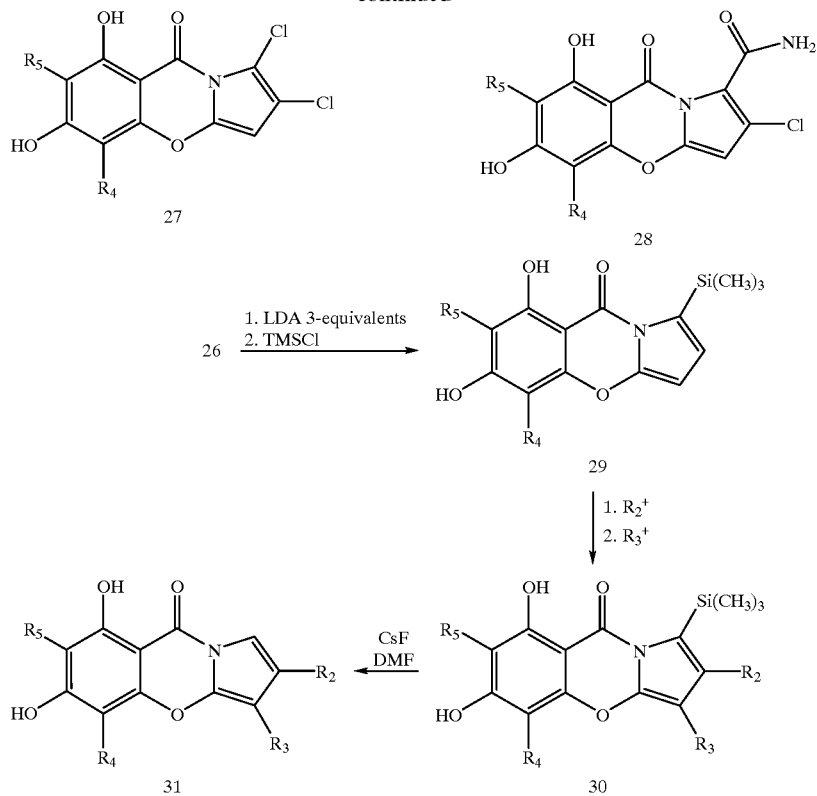
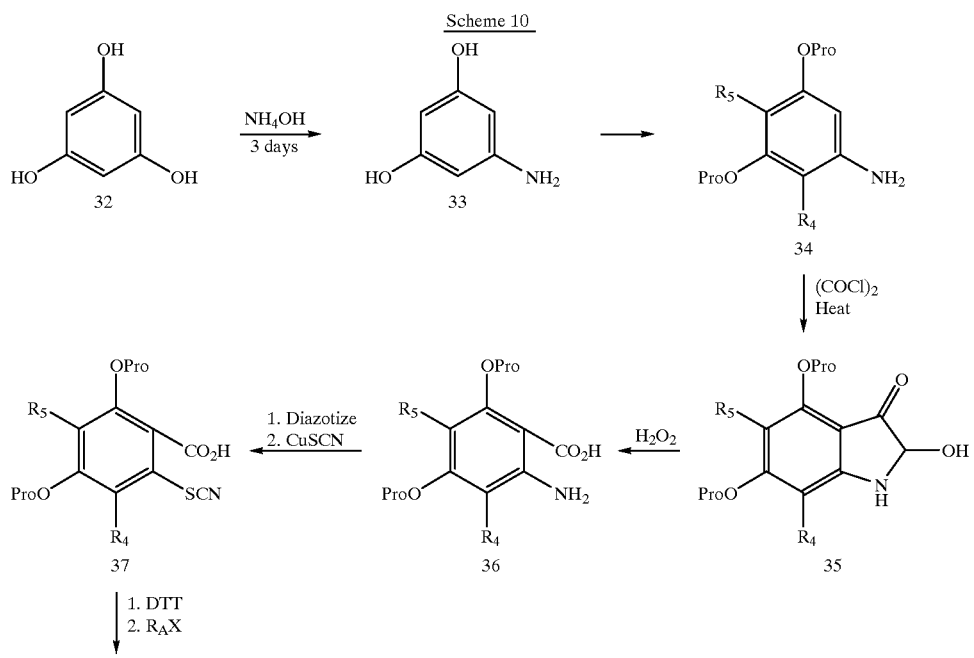

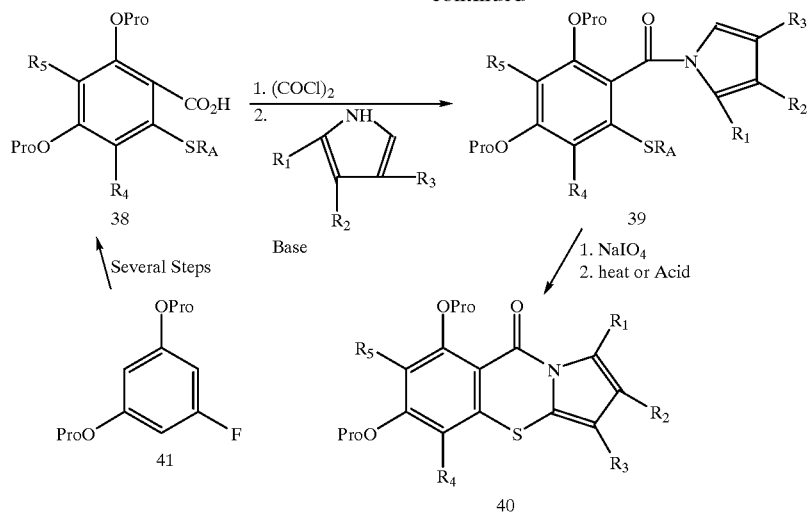
Scheme 11
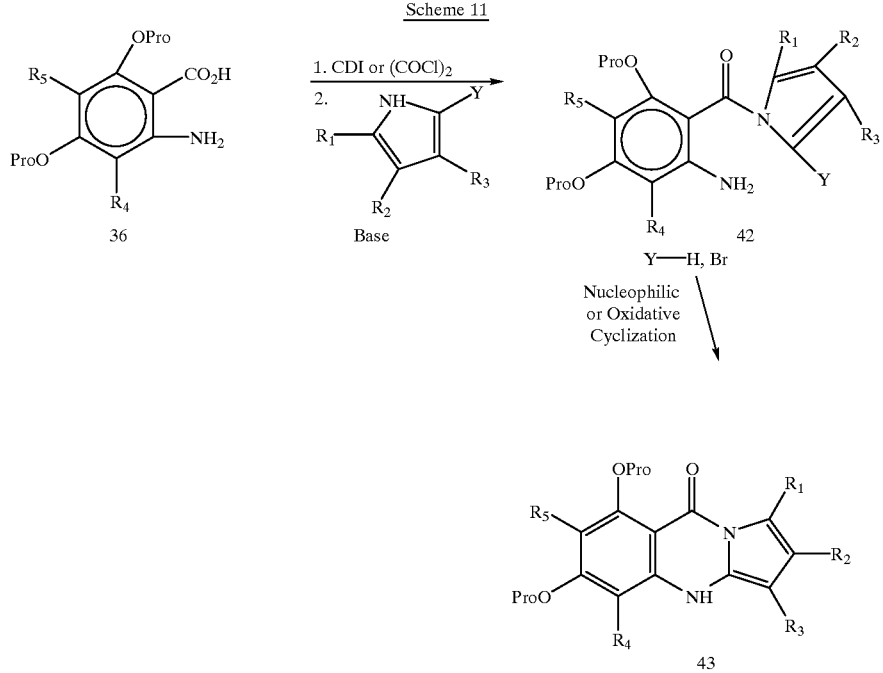

SCHEME 12

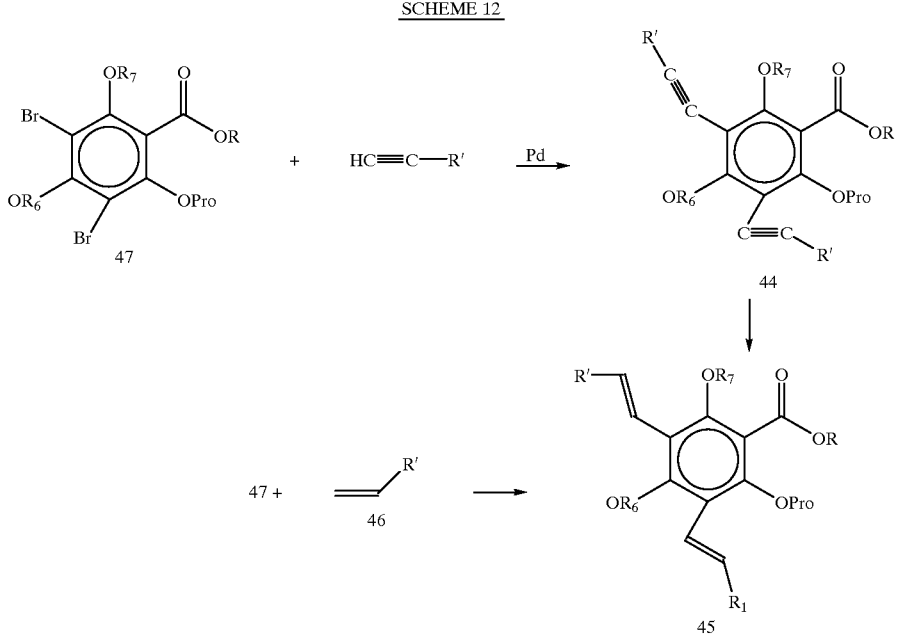

What is claimed is:

1. A compound of Formula I

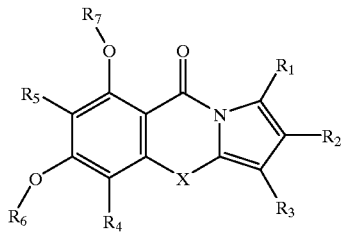

Wherein:

X is O, S or N—$R_8$;

$R_1$, $R_2$, $R_3$ and $R_8$ are independently H, straight or branched alkyl of 1–6 carbons, cycloalkyl of 3–6 carbons, alkenyl or alkynyl of from 2 to 6 atoms, phenyl or a heterocyclic ring of from 5–8 atoms with 1–3 heteroatoms as nitrogen, oxygen or sulfur, all of which rings may be optionally substituted up to 3 times by halogen, OR, $N(R)_2$, $N(R')(COR')$, CN, $CO_2R'$ or $C(O)N(R')_2$, $CO_2R$, COR, $CON(R)_2$, $CON(R'')_2$, SR, $SCO_2R$ or $SC(O)N(R)_2$;

$R_4$ is H, straight or branched alkyl of from 1–6 carbon atoms, alkenyl or alkynyl of from 2 to 6 atoms, phenyl or a heterocyclic ring of from 5–8 atoms with 1–3 heteroatoms as nitrogen, oxygen or sulfur, all of which rings may be optionally substituted up to 3 times by halogen, OR, $N(R)_2$, $N(R')COR'$, CN, $CO_2R'$ or CON $(R')_2$, $NO_2$, $N(R)_2$, N(R)COR, N(R)COR'', COR, $CO_2R$, $CON(R)_2$, $CON(R'')_2$, $N(R)CON(R)_2$, or N(R) $CO_2R$;

$R_5$ is 1–6 straight or branched alkyl, a cycloalkyl of 3–6 carbons, alkenyl or alkynyl of from 2 to 6 atoms, phenyl or heterocyclic ring of from 5–8 atoms with 1–3 heteroatoms as nitrogen, oxygen or sulfur, all of which rings may be optionally substituted up to 3 times by halogen, OR, $N(R)_2$, $N(R')COR'$, CN, $CO_2R'$ or CON $(R')_2$, OR, $N(R)_2$, N(R)COR, N(R)COR'', C(O)R, CON $(R)_2$, $CON(R'')_2$, SR or $SO_2R$;

$R_6$, $R_7$ are independently H, straight or branched alkyl of 1–6 carbons, cycloalkyl of 3–6 carbons, COR, COR'', $SO_2N(R)_2$, $C(O)N(R)_2$ and these may be optionally substituted by any of the groups listed for $R_5$;

R is H, straight or branched alkyl of 1–6 carbon atoms, cycloalkyl of from 3–6 carbon atoms, phenyl or heterocyclic ring of from 5–8 atoms with 1–3 heteroatoms as nitrogen, oxygen or sulfur, all of which may be optionally substituted by halogen, OR', $N(R')_2$, N(R') COR', CN, $CO_2R'$, $CON(R')_2$;

R' is H, alkyl of from 1–3 carbon atoms or Ph;

R'' is part of a naturally occurring amino acid connected via an amide or acyl bond as determined by the formula;

halogen is any one of fluoro, chloro, bromo or iodo;

or a pharmaceutically acceptable salt.

2. A pharmaceutical composition comprising an effective amount of the compound of claim 1, together with a pharmaceutically acceptable carrier.

3. A method of treating a mammal in need thereof comprising administering to said mammal an effective antibacterial amount of the compound of claim 1.

4. A method of inhibiting bacterial signal transduction in a mammal in need thereof comprising administering to such mammal an effective inhibiting amount of a compound of Formula I

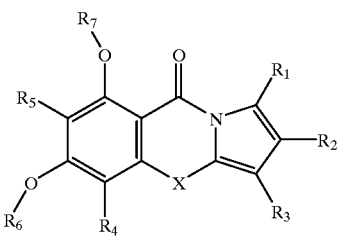

FORMULA I

Wherein:

X is O, S or N—$R_8$;

$R_1$, $R_2$, $R_3$ and $R_8$ are independently H, straight or branched alkyl of 1–6 carbons, cycloalkyl of 3–6 carbons, alkenyl or alkynyl of from 2 to 6 atoms, phenyl or a heterocyclic ring of from 5–8 atoms with 1–3 heteroatoms as nitrogen, oxygen or sulfur, all of which rings may be optionally substituted up to 3 times by halogen, OR, $N(R)_2$, $N(R')COR'$, CN, $CO_2R'$ or $CON(R')_2$, $CO_2R$, COR, $CON(R)_2$, $CON(R'')_2$, SR, $SCO_2R$ or $SC(O)N(R)_2$;

$R_4$ is H, straight or branched alkyl of from 1–6 carbon atoms, alkenyl or alkynyl of from 2 to 6 atoms, phenyl or a heterocyclic ring of from 5–8 atoms with 1–3 heteroatoms as nitrogen, oxygen or sulfur, all of which rings may be optionally substituted up to 3 times by halogen, OR, $N(R)_2$, $N(R')COR'$, CN, $CO_2R'$ or CON$(R^1)_2$, $NO_2$, $N(R)_2$, N(R)COR, N(R)COR'', COR, $CO_2R$, $C(O)N(R)_2$, $C(O)N(R'')_2$, or $N(R)CON(R)_2$, $N(R)CO_2R$;

$R_5$ is 1–6 straight or branched alkyl, a cycloalkyl of 3–6 carbons, alkenyl or alkynyl of from 2 to 6 atoms, phenyl or heterocyclic ring of from 5–8 atoms with 1–3 heteroatoms as nitrogen, oxygen or sulfur, all of which rings may be optionally substituted up to 3 times by halogen, OR, $N(R)_2$, $N(R')COR'$, CN, $CO_2R'$ or CON$(R')_2$, OR, $N(R)_2$, N(R)COR, N(R)COR'', COR, $C(O)N(R)_2$, $C(O)N(R'')_2$, SR or $SO_2R$;

$R_6$, $R_7$ are independently H, straight or branched alkyl of 1–6 carbons, cycloalkyl of 3–6 carbons, COR, COR'', $SO_2N(R)_2$, $C(O)N(R)_2$ and these may be optionally substituted by any of the groups listed for $R_5$;

R is H, straight or branched alkyl of 1–6 carbon atoms, cycloalkyl of from 3–6 carbon atoms, phenyl or heterocyclic ring of from 5–8 atoms with 1–3 heteroatoms as nitrogen, oxygen or sulfur, all of which may be optionally substituted by halogen, OR', $N[R'_2]$ $(R^1)_2$, $N(R)'C(O)R'$, CN, $CO_2R'$, $C(O)NR'_2$;

R' is H, alkyl of from 1–3 carbon atoms or Ph;

R'' is part of a naturally occurring amino acid connected via an amide or acyl bond as determined by the formula;

halogen is any one of fluoro, chloro, bromo or iodo;

or a pharmaceutically acceptable salt.

5. The compound of claim 1 wherein $R_1$, $R_2$, $R_3$, and $R_8$, are independently hydrogen, halogen, or alkyl.

6. The compound of claim 1 wherein the $R_4$ is hydrogen or alkyl.

7. The compound of claim 1 wherein the $R_5$ is alkyl.

8. The compound of claim 1 wherein the $R_6$ is hydrogen or alkyl.

9. The compound of claim 1 wherein $R_7$ is hydrogen or alkyl.

10. The compound of claim 1 wherein R is hydrogen or alkyl.

11. The compound of claim 1 wherein the heterocyclic ring is a five membered ring containing nitrogen.

12. The compound of claim 1 wherein the X is oxygen.

13. The compound of claim 1 wherein the X is nitrogen.

14. The compound of claim 1 wherein the X is sulfur.

15. The method of claim 4 wherein $R_1$, $R_2$, $R_3$, and $R_8$, are independently hydrogen, halogen, or alkyl.

16. The method of claim 4 wherein the $R_4$ is hydrogen or alkyl.

17. The method of claim 4 wherein the $R_5$ is alkyl.

18. The method of claim 4 wherein the $R_6$ is hydrogen or alkyl.

19. The method of claim 4 wherein $R_7$ is hydrogen or alkyl.

20. The method of claim 4 wherein R is hydrogen or alkyl.

21. The method of claim 4 wherein the heterocyclic ring is a five membered ring containing nitrogen.

22. The method of claim 4 wherein the X is oxygen.

23. The method of claim 4 wherein the X is nitrogen.

24. The method of claim 4 wherein the X is sulfur.

* * * * *